United States Patent [19]

Zeimer

[11] Patent Number: 4,883,061
[45] Date of Patent: Nov. 28, 1989

[54] METHOD AND APPARATUS FOR MEASURING THE THICKNESS OF EYE COMPONENTS

[75] Inventor: Ran C. Zeimer, Chicago, Ill.

[73] Assignee: The Board of Trustees of the University of Illinois, Urbana, Ill.

[21] Appl. No.: 162,011

[22] Filed: Feb. 29, 1988

[51] Int. Cl.$^4$ .............................. A61B 5/10; A61B 6/00
[52] U.S. Cl. ....................................... 128/665; 128/745; 128/774; 356/382
[58] Field of Search ............... 128/665, 666, 745, 774; 356/382

[56] References Cited

U.S. PATENT DOCUMENTS

| | | | |
|---|---|---|---|
| 3,744,916 | 7/1973 | Bey et al. | 356/382 |
| 3,807,870 | 4/1974 | Kalman | 356/382 |
| 4,125,320 | 11/1978 | Rassow et al. | 351/13 |
| 4,166,695 | 9/1979 | Hill et al. | 356/28 |
| 4,198,261 | 4/1980 | Busta et al. | 356/382 |
| 4,331,132 | 5/1982 | Mukasa | 128/745 |
| 4,346,991 | 8/1982 | Gardner et al. | 128/745 |
| 4,402,601 | 9/1983 | Riva | 356/28.5 |
| 4,454,001 | 6/1984 | Sternheim et al. | 356/382 |
| 4,502,764 | 3/1985 | Riquin | 351/160 R |
| 4,506,962 | 3/1985 | Roussel | 351/160 R |
| 4,573,778 | 3/1986 | Shapiro | 351/219 |
| 4,582,405 | 4/1986 | Muller et al. | 351/221 |
| 4,598,984 | 7/1986 | Rol | 351/219 |

OTHER PUBLICATIONS

Bodlaj et al., Applied Optics, vol. 15, No. 6, Jun., 1976, pp. 1432–1436.

Airaksinen P.J., Juvala P.S., Alanko H.I., et al.: Neuroretinal Rim Area Decrease in Ocular Hypertension and Glaucoma, Invest Ophthalmol Vis Sei 27 (Suppl): 42, 1986.

Lindsey P., Takamoto T., Lystad L.: Photogrammetric Determination of Macular Neural Retinal Thickness, Invest Ophthalmol Vis Sci 28 (Suppl): 120, 1987.

Coleman D.J. and Lizzi F.L.: In Vivo Choroidal Thickness Measurement, Am. J. Ophthalmol 88:369–375, 1979.

Sommer A., D'Anna S.A., Kwes H., et al.: High Resolution Photography of the Retinal Nerve Fiber Layer, Am. J. Ophthalmol 96: 535–539, 1983.

Primary Examiner—Francis Jaworski
Assistant Examiner—John C. Hanley
Attorney, Agent, or Firm—Marshall, O'Toole, Gerstein, Murray & Bicknell

[57] ABSTRACT

A method and apparatus for measuring the retinal or nerve fiber layer thickness. A beam of light is focused on the retina. Reflected beams from the anterior and posterior surfaces of the retina are detected and analyzed to quantitavely determine the retinal thickness.

30 Claims, 2 Drawing Sheets

METHOD AND APPARATUS FOR MEASURING THE THICKNESS OF EYE COMPONENTS

FIELD OF THE INVENTION

This invention relates to a method of and an apparatus for measuring thickness of tissue components of the eye, such as the retina, or the nerve fiber layer of the eye.

BACKGROUND OF THE INVENTION

An accurate, quantitative method to measure the nerve fiber layer or retinal thickness is greatly needed as many eye diseases are directly related to changes in these thicknesses. Eye diseases can cause the retinal tissue and the nerve fiber tissue to thin. For example, diseases such as glaucoma can produce a loss of nerve fiber in the retina. In fact, a large portion of nerve fibers can be lost before any degradation is displayed in current test methods.

Besides nerve fiber or retinal tissue thinning, eye diseases can also cause a thickening of these tissues. For example, an increase in the nerve fiber layer can result from optic disc edema, of which papilledema is one of the most common forms. Also edematous diseases of the macular region can cause retinal thickness at and around the macula to thicken. In fact, one of the early warnings of visual impairment in diabetic retinopathy, is the apparent thickening of the retina. Thus, there is a need to measure accurately and quantitatively the retinal or nerve fiber layer thickness in order to diagnose and detect diseases early, to document these diseases' progress, to assess a disease's response to therapy and to aid in prescribing follow up treatment.

Prior attempts to measure the retinal and nerve fiber layer thickness have not resulted in any acceptable quantitative methods. Clinically, one obtains an impression of the retinal thickness by one of two methods, slit lamp biomicroscopy or stereophotography.

In the first method, a narrow beam of light is directed to the desired retinal location, and its intersection with the retina is viewed stereoscopically. The separation between the images from the surface of the retina and the pigment epithelium gives the clinician an estimate of the retinal thickness. This first method is subjective and not quantitative, depends on the angle between the viewer and the illumination, only provides a subjective indication of major changes in retinal thickness, and does not provide a permanent record that can be used for follow up treatment. The second method involves stereoscopic photography and stereo viewing under magnification. This second method also is not quantitative, is not sensitive, and is prone to the variability due to changes in magnification and the stereobase. An attempt at quantitation has been made using a stereoplotter to evaluate these stereophotographs, but this method requires very expensive instrumentation, unique operator skills, and is very time consuming.

An attempt to quantitatively measure the retinal thickness noninvasively has also been attempted using scanning ultrasonography. This method has not been clinically implemented yet, probably because it is limited by the fact that the location on the fundus from which the echoes are obtained cannot accurately be determined, and very small localized areas cannot be probed because the sonar beam's focal spot is greater than half a millimeter in diameter, and most importantly the measurement cannot be performed through the crystalline lens of the eye which scatters and absorbs the sonar wave.

At present, there are also no clinical methods available to measure the thickness of the nerve fiber layer. A qualitative method to evaluate the dropout or reduction of nerve fibers has been attempted. It is based on red free photography and the examination of the appearance of the nerve fiber layer surface. This method however, is subjective, not quantitative, and relatively insensitive to small changes of the nerve fiber layer.

A growing interest has been demonstrated in the measurement of the optic disc rim area portion of the retina where the nerve fiber layer comprises a significant amount of the retina layer. Such interest has been concentrated in using stereo photography and the digitization of images. However, this method may be inaccurate because it is based on an indirect evaluation of the nerve fiber layer, since the determination of the cup edge may depend (1) on the angle at which the nerve fibers bend as they come from the retinal area into the disc, and (2) on optical artifacts such as increased scattering and/or changes in color at the rim.

It is therefore the desire of this invention to noninvasively measure eye tissue components, such as the retinal and nerve fiber layer thickness by a method and apparatus that is quantitative, accurate, operator independent, not time consuming, reproducible, easily recordable, and inexpensive.

SUMMARY OF THE INVENTION

According to this invention there is provided a method and apparatus for measuring eye tissue components, such as the retinal or nerve fiber layer thickness including the steps of providing a beam of light, focusing the beam on the retina, detecting the portion of this beam reflected from the anterior surface of the retina and detecting the portion of the beam reflected from the posterior surface of the retina, the relationship between the detected beam portions enabling the quantitative determination of the thickness of the retina. It is to be understood that "reflected" as used herein means light which is reflected, reflected and scattered, or scattered from the eye tissue components since the present invention concerns the detection of one or more of such reflected light components.

In a particular aspect of the invention the detected optimal beams are converted into respective time dependent electronic signals each having a respective maximum. The thickness of the retina is quantitatively measured by determining the time difference between the maximum of each electronic signal.

The beam of light provided may be a green coherent monochromatic beam of light. The beam diameter may also be expanded. The incoming expanded beam is always at a fixed angle with respect to the reflected beam from the retina. The projection of this beam of light onto the retina can be either a line projection or a spot projection. Converting the reflected beams into electronic signals consists in part of scanning the reflected beams with a scanning slit. The scanning slit is formed with a plurality of slits arranged radially on a scanning slit wheel. These slits are equidistant from the center in the case of point projections and are at different distances from the center in the case of line projections.

BRIEF DESCRIPTION OF THE DRAWINGS

The foregoing and other objects, features and advantages of the invention will be apparent from the following more particular description of an embodiment of the invention, as illustrated in the accompanying drawings in which like reference characters refer to the same parts throughout the different views.

DETAILED DESCRIPTION OF THE INVENTION

Figure 1:
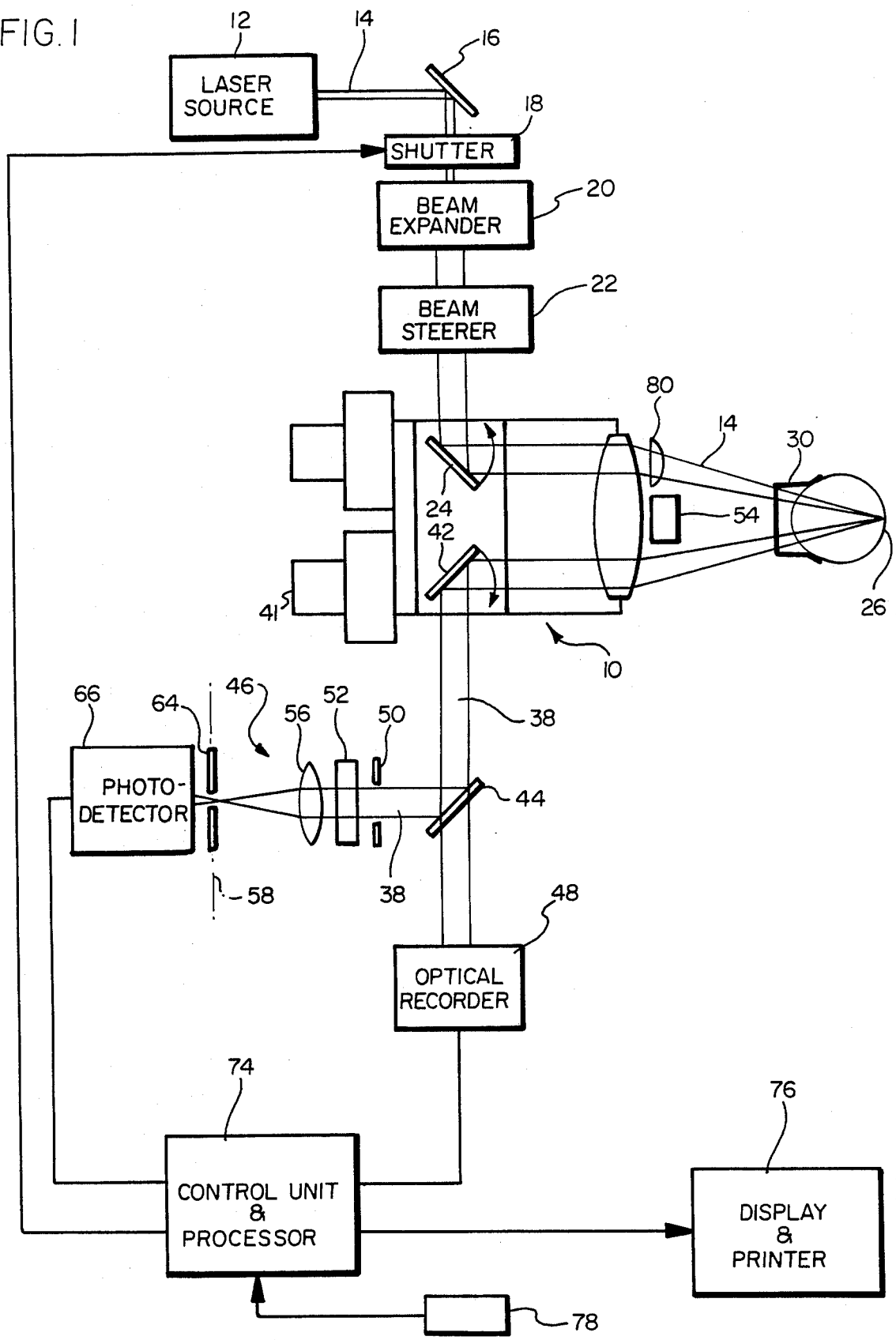
FIG. 1 is a schematic block diagram illustrating the technique of the present invention.

The apparatus of this invention as shown in FIG. 1 is mounted on a slit lamp biomicroscope 10. A green helium neon laser source (540 nm) 12 delivers a monochromatic, parallel beam of light 14. This beam of light is directed by a mirror 16 and is controlled by a shutter 18. A beam expander 20 expands the beam diameter in order to reduce the diffraction limited size of the focal spot of the laser beam on the retina. In this particular embodiment the beam is expanded to 10 mm. The beam is then directed to beam steerer 22. The expanded beam is deviated to the eye by a retractable mirror 24 and focused on the rear or fundus 26 of an eye 28 by the optics of the slit lamp biomicroscope. Mirror 24 may be retracted to allow regular operator viewing when retinal thickness measurements are not required.

Figure 2:
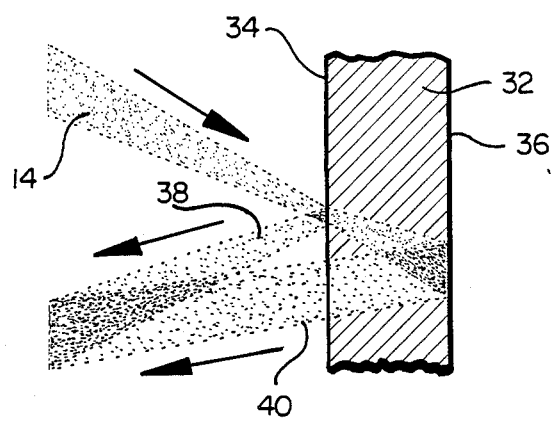
FIG. 2 is a diagram helpful in explaining the present invention and illustrating the retina of an eye with incident and reflected light beams.

A contact lens 30 with a flat surface nulls the refractive power of the cornea and does not allow the cornea to play any role in the focusing. Light beam 14 is reflected and back scattered by the posterior and anterior surfaces of the retina. Referring to FIG. 2, there is illustrated the eye fundus and particularly a portion of the retina 32 having an anterior surface 34 and a posterior surface 36. Incoming light beam 14 is reflected in a beam 38 from anterior surface 34, and also is reflected in a beam 40 from posterior surface 36. These reflected beams are picked up by the optics of the slit lamp biomicroscope and may be viewed through eye piece 41 to detect the thickness of the retina.

In the present description of an embodiment of the invention, the thickness of an eye retina is measured. It is understood that the eye tissue components can be measured, such as the nerve fiber layer, in accordance with the principles of the invention. Referring again to FIG. 1, for ease of illustration only one beam, reflected beam 38, is shown, it being understood that both reflected beams are present. Reflected beam 38 for example is directed via a retractable mirror 42 to a beam splitter 44 which splits the reflected light beam for coupling to an optoelectronic system 46 and to an optical recording system 48.

The optical recording system records the image of the reflected beams. This image is used to document the location on the retina where the current measurement is taking place through either comparison with fundus photographs (in the patient's file) recorded by other optical instruments or by comparison viewing with conventional optical systems. The optical recording system can also be used to quantitatively measure the retinal thickness as described below.

The optoelectronic system converts the reflected beams into measurable signals. The optoelectronic system contains the following components and operates as follows. An aperture stop 50 limits the reflected beam diameters to 10 mm. Narrow band pass filter 52 removes most of the illumination light which has been used to view the fundus, (such illumination light having been supplied for instance by a light source 54). Reflected light beam 38 is then focused by a lens 56 to create an image at a focal plane 58, which image represents the intersection of beam 14 with anterior surface 34 of the retina.

Figure 3A:
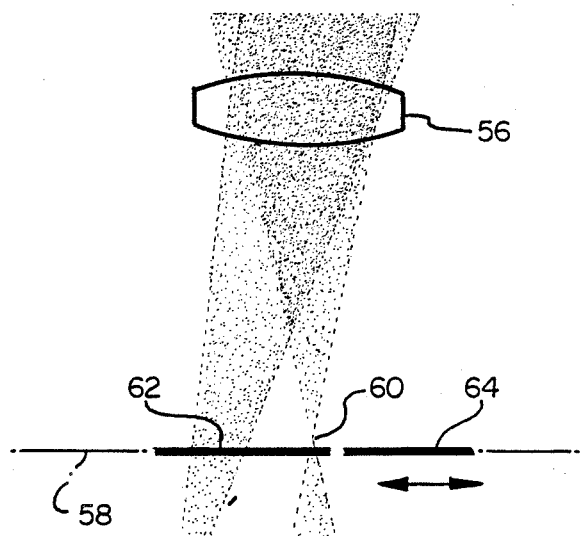
FIG. 3(a) is a diagram illustrating the reflected beams from the retina and forming the conjugated image of the retina and FIG. 3(b) is an associated plot of the electronic signal used to measure thickness of the retina.

Referring to FIG. 3(a), lens 56 focuses the reflected beams into two point images at focal plane 58. Image 60 corresponds to the intersection of the laser beam with the anterior surface of the retina and image 62 corresponds to the intersection of the laser beam with the posterior surface of the retina. The distance between these two images directly relates to the retinal thickness. A scanning slit 64 comprising a flat member with a slit is scanned across these two point images. Referring back to FIG. 1, the light corresponding to each point image that passes through scanning slit 64 will be detected by a photodetector 66.

Figure 3B:
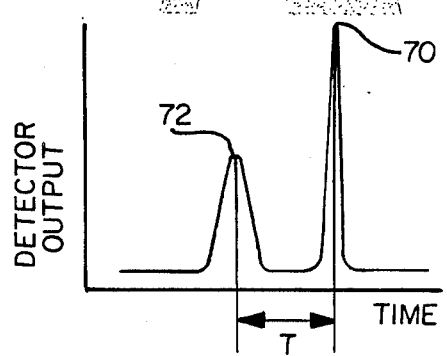

Referring to FIG. 3(b), the output of the photodetector increases as the slit coincides with the point image of the intersection of the laser beam with the retina. The slit thereby converts the point images at the focal plane into an electronic signal as a function of time. The separation in time, T, between the two maxima of the photodetector output, where maxima 70 corresponds to the intersection of the laser beam with the anterior surface of the retina (and point image 60) and maxima 72 corresponds to the intersection of the laser beam with the posterior of the retina (and point image 62), is directly related to the thickness of the tissue. Referring back to FIG. 1, the signal from the photodetector is digitized and processed by a control unit and processor 74 and the results are printed on a printer 76. The measurement can be initiated via the control unit by depressing a foot pedal 78 or other switch actuator. The control unit activates the laser shutter, the mirror 24, and the camera 48 (the optical recording system) in orderly sequence.

During data processing, the control unit, using standard programming techniques analyzes the digitized signals from the photodetector, calculates the distance between the two photodetector maxima, and converts this distance into thickness units. It will then plot the thickness of the point or spot on the retina as a function of a spot number, where the spot number corresponds to a physical location on the retina.

A profile of the thickness of a particular area of the retina may be generated. Each profile will be matched to an image of the fundus to indicate the location of the area at which a measurement was performed.

Figure 4B:
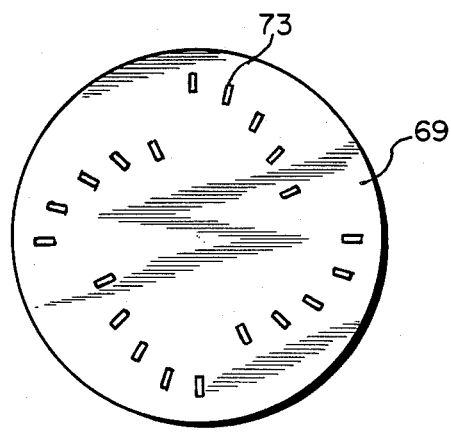
FIG. 4(a) is a plan view illustrating a scanning slit wheel used in the case of point projections on the retina and FIG. 4(b) is a plan view illustrating a scanning slit wheel used in the case of line projections on the retina.
Figure 4A:
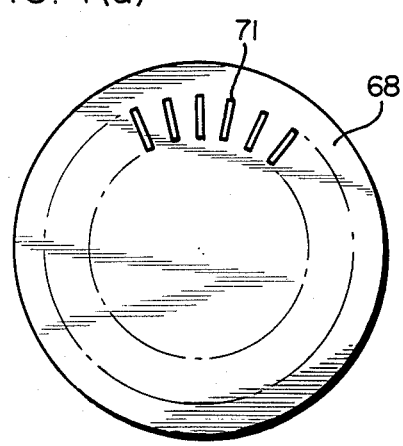

To generate the profile corresponding to the thickness of a given area location of the retina (as opposed to a spot or point location) rotating discs or wheels with a plurality of slits may be used as scanning slit 64. Referring to FIGS. 4(a) and 4(b), scanning slit is formed as a scanning slit wheel 68 or 69 which includes a series of slits arranged radially on the wheel. The wheel rotates at a constant speed. FIG. 4(a) shows a scanning slit wheel 68 with a plurality of elongated radial slits 71 arranged circularly around the wheel; and FIG. 4(b) shows a scanning slit wheel 69 with a plurality of shorter radial slits 73 arranged in a precise pattern around the wheel.

The profile of the thickness of the retina area location may be generated either:

(1) by acquiring data relating to a series of single laser points projected on the retina produced by the beam steering mechanism moving the laser beam along a predetermined path. The beam steering mechanism is controlled by the control unit. In the case of a series of point projections, each slit 71 on wheel 68, as seen in FIG. 4(a), will be equidistant from the center of the wheel; or (2) from the acquisition of data corresponding to numerous spots on a line projected on the retina by a cylindrical lens 80, which lens is placed in the path of light beam 14 between the biomicroscope optics and the contact lens. In the case of a line projection, each slit 73 on wheel 69, as seen in FIG. 4(b), will be located at a different distance from the center of the wheel thereby corresponding to a different spot along the line.

If data acquisition is accomplished by projecting a series of single points, the cylindrical lens is removed from the system, and the beam steering mechanism is activated. If the data acquisition is done by projecting a line, the beam steering mechanism is inactive and the cylindrical lens is employed. These data acquisitions can either be obtained on-line as described above, or from the recorded fundus image recorded by the optical recording system.

If the optical recording system employed is a photographic camera, a microdensitometer can be scanned across the image on the film and translate the variation in grey density into signals similar to those generated by the photodetector above. If the optical recording system employed is a video camera, the recorded video image could be digitized and the image could be analyzed pixel by pixel to yield a similar profile. If the beam steering option is chosen, the exposure time of the optical recording system will be increased to record all the spots along the path.

The thickness measurement will require the following actions: dilating the patient's pupil; anesthetizing the patient's cornea; applying a contact lens to the eye; aiming the laser to the point of interest on the fundus; and depressing the foot pedal or other actuator. The following examples are presented to illustrate the applicability of the present invention for the intended purposes of measuring the thickness of tissue components of the eye. Example I concerns an actual eye and Example II concerns a model eye.

EXAMPLE I

A measurement of the retinal thickness has been performed using the system of the preferred embodiment of this invention. This system included a green helium neon laser with a power of 56 microwatts, a shutter, and a 5X expander. The laser beam was focused on the fundus of the eye using the optics of a Zeiss slit lamp biomicroscope. The reflected beams were recorded by the optical recording system which was composed of a 35 mm camera loaded with Kodak Tri-X 400 ASA film. The exposure time for each photograph was ⅛ of a second. A cylindrical lens was placed between the optics of a slit lamp biomicroscope and the eye converting the light beam into a line illumination on the eye. This line was 2.3 mm in length on the retina. The fundus background was recorded with an illumination lamp. The eye was dilated, a flat contact lens was placed on the eye after a drop of anesthetic was applied to the eye, and a series of photographs were taken at different location on the fundus.

A densitometric scan was obtained with a microdensitometer. A slit was scanned across the image, in this case the image on the film negative obtained by the 35 mm camera. The light that passed through this slit was detected by a phototransistor. From the scan of the detected variation in light intensity, a discernible thickness was obtained.

EXAMPLE II

The feasibility and the accuracy of the present invention was tested using a model eye. The eye was represented by a lens, which had a focal length of 17 mm. In air, this focal length was equivalent to the 25-mm ocular focal length. A realistic, dilated pupil, 6 mm in diameter, was introduced behind the lens. To simulate the transparent retina, clear plastics were placed at the focal plane. A helium-neon laser delivered, via a mirror, a parallel beam to the model eye. The scattered and reflected light passed through an effective pupillary entrance of 1 mm, separated 4 mm from the incoming beam. This reflected light was focused by another lens onto the plane of the scanning slit. A 10 micrometer slit was held on a rod fixed to a loudspeaker driven by a waveform generator. The light that passed through the slit was detected by a phototransistor. The signal was stored and digitized by a Data Precision waveform analyzer. The distance between the two peaks generated was measured and used to quantitate the thickness.

Thickness measurements were performed on targets with five different thicknesses. The separation at the image plane was plotted as a function of the thickness of the material. The data demonstrated that the separation is linearly dependent on the thickness, with an excellent correlation factor ($r > 0.9999$). By computing the standard deviation of five measurements that were performed after moving the target and refocusing it, reproducibility of less than ±9 micrometers for thicknesses between 150 and 500 micrometers was obtained. Three plastic targets with different thicknesses were measured after the correlation curve was obtained. Each target was measured 4 times, and the mean was computed. The accuracy was found to be 5.5 micrometers.

While the above described embodiments are in accordance with the present invention, it is understood that the same is not limited thereto, but is susceptible of numerous changes as known to a person skilled in the art, and therefore this invention is not limited to the details shown and described herein, but intended to cover all such changes and modifications as are obvious to one of ordinary skill in the art.

What is claimed is:

1. Apparatus for enabling the determination of the thickness of the retina of an eye between the anterior surface and the posterior surface of the retina, said apparatus comprising:

a light source providing a coherent monochromatic beam;

means for focusing said beam on the retina to provide a first reflected beam reflected from the anterior surface of the retina and a second reflected beam reflected from the posterior surface of the retina; and detection means for detecting said first reflected beam and said second reflected beam, wherein the relationship between said first and second reflected beams enables the determination of the thickness of the retina.

2. Apparatus according to claim 1, wherein said light source includes means providing a green coherent monochromatic beam of light.

3. Apparatus according to claim 1, wherein said means for focusing said beam includes means for expanding the diameter of said beam and means for transferring the expanded beam at a fixed angle to said retina with respect to said beams reflected from said retina.

4. The apparatus of claim 1, wherein said first portion of said beam corresponds to a first optic image and said second portion of said beam corresponds to a second optic image and wherein said detection means include:
means for scanning said first and second optic images to provide said optic images as a function of time; and
means for converting said optic images as a function of time into electronic signals corresponding to the thickness of the retina.

5. The apparatus of claim 4, wherein said means for focusing includes means for steering said beam to different portions of the retina.

6. The apparatus of claim 4, wherein said means for focusing includes means for projecting said beam into a line illumination on the retina.

7. The apparatus of claim 5, wherein said means for scanning includes a constant speed slit wheel having a plurality of elongated radial slits with each slit being equidistant from the center of said slit wheel.

8. The apparatus of claim 1, wherein said means for focusing includes means for providing a light source for illuminating the fundus of the eye.

9. The apparatus of claim 1, wherein said detection means includes means for recording said first and second reflected beams.

10. Apparatus for determining the thickness of the retina of an eye between the anterior surface and the posterior surface of the retina, said apparatus comprising:
a light source providing a coherent monochromatic beam;
means for focusing said beam on the retina to provide a first reflected beam reflected from the anterior surface of the retina and a second reflected beam reflected from the posterior surface of the retina;
detection means for detecting said first reflected beam and said second reflected beam, wherein the relationship between said first and second reflected beams enables the determination of the thickness of the retina; and
means for measuring the relationship between said first and second reflected beams for determining the thickness of the retina.

11. The apparatus of claim 10, wherein said first reflected beam corresponds to a first optic image and said second reflected beam corresponds to a second optic image, and wherein said detection means and means for measuring include,
means for scanning said first and second optic images to provide said optic images as a function of time;
means for converting said first and second optic images as a function of time into respective first and second time dependent electronic signals having a respective maximum;
means for determining the time position of the respective maximum of each of said first and second time dependent electronic signals; and
means for measuring the time difference between said respective time positions, said time difference corresponding to the distance between the anterior and the posterior surfaces corresponding to the thickness of said retina.

12. The apparatus of claim 10, for determining the thickness of said retina at different portions of the retina, including means for consecutively steering said beam to said different portions of the retina and means for respectively detecting and measuring the relationship between said first and second reflected beams corresponding to said different portions of the retina for determining the thickness of said retina at each of said different portions of the retina.

13. The apparatus of claim 10, for determining the thickness of said retina at different portions of the retina, including means for projecting said beam into a line illumination on the retina and means for detecting and measuring the respective first and second reflected beams corresponding to said different portions of the retina for determining the thickness of said retina at each of said different portions of the retina.

14. Apparatus for enabling the determination of the thickness of the retina of an eye between the anterior surface and the posterior surface of the retina, said apparatus comprising:
a light source providing a coherent monochromatic beam;
means for focusing said beam on the retina to provide a first reflected beam reflected from the anterior surface of the retina and a second reflected beam reflected from the posterior surface of the retina;
detection means for detecting said first reflected beam and said second reflected beam, wherein the relationship between said first and second reflected beams enables the determination of the thickness of the retina;
wherein said means for focusing and said detection means includes a slit lamp biomicroscope and means for nulling the refractive power of the cornea of said eye, and means for viewing said first and second reflected beams through said slit lamp biomicroscope.

15. Apparatus for enabling the determination of the thickness of the retina of an eye between the anterior surface and the posterior surface of the retina, said apparatus comprising:
a light source providing a coherent monochromatic beam;
means for focusing said beam into a line illumination on the retina to focus on sequentially different portions of the retina along said line illumination and thereby sequentially provide respectively a first reflected beam reflected from the anterior surface of the retina and a second reflected beam reflected from the posterior surface of the retina;
detection means for sequentially detecting respectively said first reflected beam and said second reflected beam, wherein the relationship between said respective first and second reflected beams enables the sequential determination of the thickness of the retina at said sequentially different portions of the retina;
said respective first reflected beam corresponding to a first optic image and said respective second reflected beam corresponding to a second optic image and wherein said detecting means includes, means for scanning said first and second optic images to provide optic images as a function of time; and means for converting said optic images as a function of time into electronic signals corresponding to the thickness of the retina;

wherein said means for scanning includes a constant speed slit wheel having at least one pattern including a plurality of slits with each slit in said pattern being at a different distance from the center of said slit wheel.

16. A method of enabling the determination of the thickness of the retina of an eye between the anterior surface and the posterior surface of the retina, said method comprising the steps of:

providing a beam of coherent monochromatic light; focusing said beam on the retina; and detecting a first portion of said beam reflected from the anterior surface of said retina and a second portion of said beam reflected from the posterior surface of said retina, wherein the relationship between said first and second portions of said beam enable the determination of the thickness of the retina.

17. The method of claim 16, wherein there is provided a beam of green coherent monochromatic light.

18. The method of claim 16, wherein said focusing includes expanding the diameter of said beam and transferring the expanded beam at a fixed angle to said retina with respect to said beam portions reflected from said retina.

19. The method of claim 18, wherein said first portion of said beam corresponds to a first optic image and said second portion of said beam corresponds to a second optic image and wherein said detecting includes:

converting said first and second optic images as a function of time into respective electronic signals, wherein the time difference between said respective electronic signals corresponds to the thickness of the retina.

20. The method of claim 19, including steering said beam to focus on sequentially different portions of the retina and sequentially detecting said respective first and second portions of said beam corresponding to said sequentially different portions of the retina to enable the determination of the thickness of the retina at said sequentially different portions of the retina.

21. The method of claim 19, wherein said focusing includes projecting said beam into a line illumination of sequentially different portions of the retina, and sequentially detecting said respective first and second portions of said beam corresponding to said sequentially different portions of the retina along said line illumination to enable the determination of the thickness of the retina at said sequentially different portions of the retina along said line illumination.

22. The method of claim 18, wherein said focusing includes providing a light source for illuminating the fundus of the eye.

23. The method of claim 16, wherein said detecting includes recording said first and second portions of said beam by forming a permanent image representing a portion of the retina.

24. The method of claim 16, wherein said detecting includes providing the optics of a slit lamp biomicroscope and nulling the refractive power of the cornea of said eye, and viewing said first and second portions of said beam through said optics.

25. A method of enabling the determination of the thickness of the retina of an eye between the anterior surface and the posterior surface of the retina, said method comprising the steps of:

providing a beam of coherent monochromatic light; focusing said beam on the retina;

detecting a first portion of said reflected from the anterior surface of said retina and a second portion of said beam reflected from the posterior surface of said retina, wherein the relationship between said first and second portions of said beam enable the determination of the thickness of the retina; and measuring the relationship between said first and second portions of said beam to determine the thickness of the retina.

26. The method of claim 25, wherein said first portion of said beam corresponds to a first optic image and said second portion of said beam corresponds to a second optic image and wherein said detecting and measuring includes:

scanning said first and second optic images to provide corresponding optic information as a function of time;

converting said optic information into respective first and second time dependent electronic signals each having a respective maximum;

determining the time position of the respective maximum of each of said first and second time dependent electronic signals; and measuring the time difference between said respective time positions, said time difference corresponding to the distance between the anterior and the posterior surfaces corresponding to the thickness of said retina.

27. The method of claim 25 for determining the thickness of said retina at different portions of the retina, including consecutively steering said beam to said different portions of the retina and respectively detecting and measuring the relationship between said respective first and second portions of said beam corresponding to said different portions of the retina for determining the thickness of said retina at each of said different portions of the retina.

28. The method of claim 25, for determining the thickness of said retina at different portions of the retina, including projecting said beam into a line illumination on the retina and detecting and measuring the relationship between said respective first and second portions of said beam corresponding to said different portions of the retina along said line illumination for determining the thickness of said retina at each of said different portions of the retina along said line illumination.

29. The method of claim 25, wherein said detecting includes recording said first and second portions of said beam on a recording medium, and said measuring includes determining the thickness of the retinal using the recorded first and second portions of said beam.

30. A method of enabling the determination of the thickness of the retina of an eye between the anterior surface and the posterior surface of the retina, said method comprising the steps of:

providing a beam of coherent monochromatic light; focusing said beam on the retina, including expanding the diameter of said beam and transferring the expanded beam at a fixed angle to said retina with respect to said beam portions reflected from said retina, wherein said first portion of said beam corresponds to a first optic image and said second portion of said beam corresponds to a second optic image; and detecting a first portion of said beam reflected from the anterior surface of said retina and a second portion of said beam reflected from the posterior surface of said retina, wherein the relationship between said first and second portions of said beam enable the determination of the thickness of the retina, including converting said first and second optic images as a function of time into respective electronic signals by slit scanning said optic images, wherein the time difference between said respective electronic signals corresponds to the thickness of the retina.

* * * * *

UNITED STATES PATENT AND TRADEMARK OFFICE
CERTIFICATE OF CORRECTION

PATENT NO. : 4,883,061

DATED : November 28, 1989

INVENTOR(S) : Zeimer

It is certified that error appears in the above-identified patent and that said Letters Patent is hereby corrected as shown below:

Col. 10, line 9, change "of said reflected" to --of said beam reflected--

Signed and Sealed this

Twenty-third Day of July, 1991

Attest:

HARRY F. MANBECK, JR.

*Attesting Officer*  *Commissioner of Patents and Trademarks*